United States Patent [19]

Holloway et al.

[11] Patent Number: 5,120,766

[45] Date of Patent: Jun. 9, 1992

[54] THERAPEUTIC USES OF 2-(PHENOXYPROPANOLAMINO)ETHOXY-PHENOXYACETIC ACID DERIVATIVES

[75] Inventors: Brian R. Holloway, Congleton; Jacqueline M. Jackson, Rudyard, both of England

[73] Assignee: Imperial Chemical Industries PLC, London, England

[21] Appl. No.: 612,910

[22] Filed: Nov. 14, 1990

[30] Foreign Application Priority Data

Nov. 17, 1989 [GB] United Kingdom ............... 8926083

[51] Int. Cl.⁵ ............... A61K 31/195; A61K 31/165
[52] U.S. Cl. ............................. 514/620; 514/824; 514/567
[58] Field of Search ............... 514/619, 620, 622, 623, 514/824, 652, 567

[56] References Cited

U.S. PATENT DOCUMENTS 4,772,631 9/1988 Holloway et al. ............... 514/539
4,927,836 5/1990 Holloway et al. ............... 514/620
4,977,148 12/1990 Holloway et al. ............... 514/183

FOREIGN PATENT DOCUMENTS 244062 11/1987 European Pat. Off. .

OTHER PUBLICATIONS

Goodman and Gilman's "The Pharmacological Basis of Therapeutics", pp. 827-845, 1985.

*Primary Examiner*—Frederick E. Waddell
*Assistant Examiner*—Kimberly R. Jordan
*Attorney, Agent, or Firm*—Cushman, Darby & Cushman

[57] ABSTRACT

The use of a compound of the formula (I):

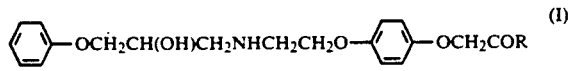

wherein R is hydroxy or 2-methoxyethylamino or a pharmaceutically acceptable salt thereof, in lowering triglyceride and/or cholesterol levels and/or increasing high density lipoprotein levels. These compounds may be used in treating hypertriglycerdaemia, hypercholesterolaemia, conditions of low HDL (high density lipoprotein) levels and atherosclerotic disease.

12 Claims, No Drawings

THERAPEUTIC USES OF 2-(PHENOXYPROPANOLAMINO)ETHOXY-PHENOXYACETIC ACID DERIVATIVES

The present invention relates to 2-(phenoxypropanolamino)-ethoxyphenoxyacetic acid derivatives and in particular to the use of such derivatives in the therapeutic treatment of animals including humans. These derivatives lower triglyceride levels and cholesterol levels and raise high density lipoprotein levels are therefore of use in combatting medical conditions wherein such lowering (and raising) is thought to be beneficial. Thus they may be used in the treatment of hypertriglyceridaemia, hypercholesterolaemia and conditions of low HDL (high density lipoprotein) levels in addition to the treatment of atherosclerotic disease such as of coronary, cerebrovascular and peripheral arteries, cardiovascular disease and related conditions. The compounds for use in the methods of the present invention cause relatively little cardiac stimulation and/or other side-effects such as lack of peripheral effect on the vascular system. Selectivity of effect is beneficial in the treatment of the above medical conditions.

Accordingly the present invention provides a method of lowering triglyceride and/or cholesterol levels and/or increasing high density lipoprotein levels which comprises administering, to an animal in need thereof, a therapeutically effective amount of a compound of the formula (I):

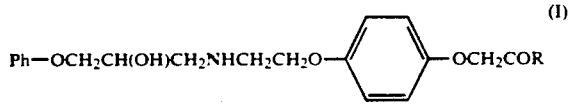

wherein R is hydroxy or 2-methoxyethylamino or a pharmaceutically acceptable salt thereof.

In another aspect the present invention provides the use of the compound of the formula (I) or a pharmaceutically acceptable salt thereof for the manufacture of a medicament for lowering triglyceride and/or cholesterol levels, and/or increasing high density lipoprotein levels.

In a further aspect the present invention provides a method of treating atherosclerosis which comprises administering, to an animal in need thereof, a therapeutically effective amount of a compound of the formula (I).

In yet a further aspect the present invention provides the use of the compound of the formula (I) or a pharmaceutically acceptable salt thereof for the manufacture of a medicament for treating atherosclerosis.

Preferably in the compounds of the formula (I) R is 2-methoxyethylamino.

The compounds of the formula (I) contain an asymmetric carbon atom and can exist as an optically active enantiomer (R or S according to the Cahn-Ingold-Prelog convention) or as an optically inactive racemate. The compounds for use in the present invention contain at least some of the laevorotatory optically active form (−) which corresponds to (S) absolute configuration. Conveniently the compounds for use in the present invention are provided as the racemate but preferably are provided as the laevorotatory optically active form (−).

The compounds of formula I are basic and may be isolated and used either in the form of a free base or of a pharmaceutically acceptable acid-addition salt thereof. In addition, the compound of the formula (I) wherein R is hydroxy is amphoteric and may be isolated and used in the zwitterionic form, or as a pharmaceutically acceptable acid-addition salt, or as a salt with a base affording a pharmaceutically acceptable cation.

Particular examples of pharmaceutically acceptable acid-addition salts include, for example, salts with inorganic acids such as hydrohalides (especially hydrochlorides or hydrobromides), sulphates and phosphates, and salts with organic acids such as the free acid form of sulphonated polystyrene.

Particular examples of salts with bases affording a pharmaceutically acceptable cation include, for example, alkali metal and alkaline earth metal salts, such as sodium, potassium, calcium and magnesium salts, and ammonium salts and salts with suitable organic bases, such as triethanolamine.

A preferred compound for use in the methods of the present invention is:
(S)-4-[2-(2-hydroxy-3-phenoxypropylamino)ethoxy]-N-(2-methoxyethyl)-phenoxyacetamide hydrochloride.

The compound of the formula (I) and pharmaceutically acceptable salts thereof wherein R is hydroxy are known from, and/or can be prepared by, the methods of European Patent Application Publication No 210849. The compounds of the formula (I) and pharmaceutically acceptable salts thereof wherein R is 2-methoxyethylamino are known from, and/or can be prepared by, the methods of European Patent Application Publication No 254532.

The compounds of the formula (I) and their pharmaceutically acceptable salts are known as thermogenic agents, that is they stimulate thermogenesis in warm-blooded animals and are of use, for example, in the treatment of obesity and related conditions, such as obesity of mature onset diabetes. These compounds may also be of value in the modification of carcass composition, for example, by increased catabolism of fat in meat producing animals, such as cattle, pigs, sheep, goats and/or rabbits.

We have now discovered that the compounds of the formula (I) and their pharmaceutically acceptable salts lower triglyceride and/or cholesterol levels and/or increase HDL levels and are therefore of use in treating disease conditions such as atherosclerosis.

In order to use the compounds of the formula (I) and pharmaceutically acceptable salts thereof for the lowering of triglyceride and/or cholesterol levels and/or increasing HDL levels they are normally formulated in accordance with standard pharmaceutical practice as a pharmaceutical composition.

The pharmaceutical compositions of this invention may be administered in standard manner for example by oral or parenteral administration. For these purposes they may be formulated by means known to the art into the form of, for example, tablets, capsules, pills, powders, aqueous or oily solutions or suspensions, emulsions, and sterile injectable aqueous or oily solutions or suspensions.

In general compositions for oral administration are preferred.

The compositions may be obtained using standard excipients and procedures well known in the art. A unit dose form such as a tablet or capsule will usually contain, for example 0.1–250 mg of active ingredient. The compositions may also contain other active ingredients known for use in the treatment of atherosclerosis and related conditions, for example:

- fibrates such as clofibrate, bezafibrate and gemfibrozil;
- inhibitors of cholesterol biosynthesis such as HMG-CoA reductase inhibitors for example lovastatin, simvastatin and pravastatin;
- inhibitors of cholesterol absorption for example beta-sitosterol and (acyl CoA:cholesterol acyltransferase) inhibitors for example melinamide;
- anion exchange resins for example cholestyramine, colestipol or dialkylaminoalkyl derivatives of a cross-linked dextran;
- nicotinyl alcohol, nicotinic acid or a salt thereof;
- vitamin E; and
- thyromimetics.

When used to produce triglyceride- and/or cholesterol-lowering, and/or increasing high density lipoprotein levels, in warm-blooded animals including man, a compound of the formula (I) or a pharmaceutically acceptable salt will be administered so that a dose in the general range 0.002-20 mg/kg, and preferably in the range 0.02-10 mg/kg, is administered daily, given in a single dose or divided doses as necessary. However, it will be appreciated by those skilled in the art that the dosage will necessarily be varied as appropriate, depending on the severity of the condition under treatment and on the age and sex of the patient and according to known medical principles.

The effects of a representative compound for use in a method according to this invention are described in the following Example:

EXAMPLE 1

(S)-4-[2-(2-Hydroxy-3-phenoxypropylamino)ethoxy]-N-(2-methoxyethyl)-phenoxyacetamide hydrochloride was administered to a group of 5 male obese Zucker rats (approximately 18 weeks old) in a powdered diet for 27 days. The rate of administration was 3 mg/Kg/day (per body weight of rat). A control group of 5 obese Zucker rats was also studied. On the 28th day food was removed and the rats were fasted for 24 hours. 8 hours into the fasting period the treated rats were dosed, by gavage, with a suspension of the above compound (3 mg/Kg) in 0.025% aqueous polysorbate. The control rats received excipient alone. 16 hours later the rats were anaesthetised and a blood sample taken from the dorsal aorta.

Plasma triglyceride levels were assayed using a Sigma 320-A assay kit.

|  | Dose level (mg/Kg) | Triglyceride levels (mg/dl) |
|---|---|---|
| Control rats | 0 | 581 |
| Treated rats | 3 | 311* |

*Significance P < 0.001

EXAMPLE 2

(S)-4-[2-(2-Hydroxy-3-phenoxypropylamino)ethoxy]-N-(2-methoxyethyl)phenoxyacetamide hydrochloride was administered to a group of 36 beagle dogs aged between 35 and 40 weeks divided into groups. Male dogs weighed between 15.2 and 19.0 kg; female dogs weighed between 12.9 and 16.2 kg.

Blood samples (2 ml in lithium heparin anticoagulant) were taken twice before the study and then during the fourth week of dosing. These samples were tested for triglyceride levels and results were as follows:

| Triglyceride levels (mmol/l) | | | | |
|---|---|---|---|---|
| Day | Group I (control) | Group II (10 mg/kg) | Group III (30 mg/kg) | Group IV (100 mg/kg) |
| −23* | 0.410 | 0.379 | 0.373 | 0.360 |
| −13* | 0.382 | 0.333 | 0.303 | 0.303 |
| +23 | 0.380 | 0.297 | 0.318 | 0.275 |

*i.e. before commencement of study.

In comparable studies in dogs over six months the following results were obtained:

| Week | Group I (control) | Group II (5 mg/kg) | Group III (25 mg/kg) | Group IV (125 mg/kg) |
|---|---|---|---|---|
| −4* | 0.369 | 0.359 | 0.371 | 0.412 |
| −2* | 0.314 | 0.371 | 0.402 | 0.358 |
| +13 | 0.372 | 0.275 | 0.252 | 0.197 |
| +25 | 0.432 | 0.280 | 0.338 | 0.242 |

These samples were also tested for cholesterol levels and the results were as follows:

| Cholesterol levels (mmol/l) | | | | |
|---|---|---|---|---|
| Week | Group I (control) | Group II (10 mg/kg) | Group III (30 mg/kg) | Group IV (100 mg/kg) |
| −23* | 4.63 | 4.44 | 4.88 | 5.08 |
| −13* | 4.57 | 4.46 | 4.88 | 5.23 |
| +23 | 4.33 | 3.87 | 3.95 | 3.72 |
| Week | Group I (control) | Group II (5 mg/kg) | Group III (25 mg/kg) | Group IV (125 mg/kg) |
| −4* | 4.43 | 4.05 | 4.20 | 4.11 |
| −2* | 4.85 | 4.28 | 4.73 | 4.14 |
| +13 | 4.58 | 3.63 | 3.59 | 2.93 |
| +25 | 4.72 | 4.04 | 3.80 | 3.44 |

These samples were further tested for free fatty acid levels and the results were as follows:

| Free fatty acid levels (mmol/l) | | | | |
|---|---|---|---|---|
| Week | Group I (control) | Group II (10 mg/kg) | Group III (30 mg/kg) | Group IV (100 mg/kg) |
| −23* | 0.90 | 0.94 | 0.45 | 0.52 |
| −13* | 0.77 | 0.74 | 0.57 | 0.61 |
| +23 | 0.70 | 0.34 | 0.26 | 0.23 |
| Week | Group I (control) | Group II (5 mg/kg) | Group III (25 mg/kg) | Group IV (125 mg/kg) |
| −4* | 0.650 | 0.796 | 0.808 | 0.652 |
| −2* | 0.563 | 0.696 | 0.706 | 0.559 |
| +13 | 0.675 | 0.370 | 0.180 | 0.315 |
| +25 | 0.694 | 0.476 | 0.350 | 0.297 |

We claim:

1. A method of lowering triglyceride and/or cholesterol levels and/or increasing high density lipoprotein levels which comprises administering to a patient in need thereof an effective amount of a compound of the formula (I)

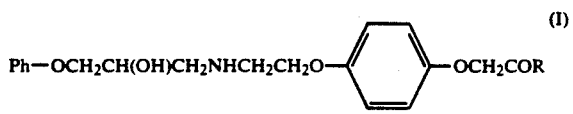

Ph—OCH$_2$CH(OH)CH$_2$NHCH$_2$CH$_2$O—⟨ ⟩—OCH$_2$COR  (I)

wherein R is hydroxy or 2-methoxyethylamino or a pharmaceutically acceptable salt thereof.

2. A method of treating atherosclerosis which comprises administering to a patient in need thereof an effective amount of a compound of the formula (I)

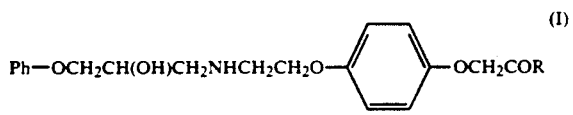
(I)

wherein R is hydroxy or 2-methoxyethylamino or a pharmaceutically acceptable salt thereof.

3. A method of treating hypertriglyceridaemia which comprises administering to a patient in need thereof an effective amount of a compound of the formula (I)

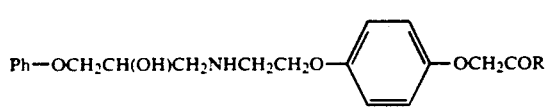
(I)

wherein R is hydroxy or 2-methoxyethylamino or a pharmaceutically acceptable salt thereof.

4. A method of treating hypercholesterolaemia which comprises administering to a patient in need thereof an effective amount of a compound of the formula (I)

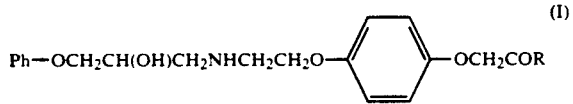
(I)

wherein R is hydroxy or 2-methoxyethylamino or a pharmaceutically acceptable salt thereof.

5. A method of treating conditions of low HDL levels which comprises administering to a patient in need thereof an effective amount of a compound of the formula (I)

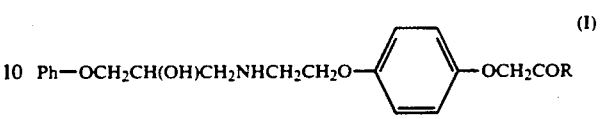
(I)

wherein R is hydroxy or 2-methoxyethylamino or a pharmaceutically acceptable salt thereof.

6. A method according to any one of claims 1 to 5 wherein the compound of the formula (I) or pharmaceutically acceptable salt thereof is in the laevorotatory optically active form (−).

7. A method according to any one of claims 1 to 5 wherein R is 2-methoxyethylamino.

8. A method according to claim 6 wherein R is 2-methoxyethylamino.

9. A method according to any one of claims 1 to 5 wherein the compound of the formula (I) is (S)-4-[2-(2-hydroxy-3-phenoxypropylamino)ethoxy]-N-(2-methoxyethyl)phenoxyacetamide hydrochloride.

10. A method according to claim 6 wherein the compound of the formula (I) is (S)-4-[2-(2-hydroxy-3-phenoxypropylamino)ethoxy]-N-(2-methoxyethyl)-phenoxyacetamide hydrochloride.

11. A method according to any one of claims 1 to 5 wherein the medicament is suitable for oral administration.

12. A method according to claim 6 wherein the medicament is suitable for oral administration.

* * * * *